United States Patent [19]

Dickakian

[11] Patent Number: 4,781,893

[45] Date of Patent: * Nov. 1, 1988

[54] APPARATUS FOR DETERMINING FOULING TENDENCY OF LIQUID HYDROCARBONS USING POLAR POLYMERIC MEMBRANES

[75] Inventor: Ghazi B. Dickakian, Kingwood, Tex.

[73] Assignee: Exxon Chemicals Patents Inc., Linden, N.J.

[*] Notice: The portion of the term of this patent subsequent to Nov. 1, 2005 has been disclaimed.

[21] Appl. No.: 24,730

[22] Filed: Mar. 11, 1987

Related U.S. Application Data

[63] Continuation-in-part of Ser. No. 910,910, Sep. 24, 1986, which is a continuation-in-part of Ser. No. 830,386, Feb. 18, 1986, which is a continuation-in-part of Ser. No. 723,598, Apr. 15, 1985.

[51] Int. Cl.$^4$ ............... G01N 21/17; G01N 30/90; G01N 33/26

[52] U.S. Cl. ................... 422/69; 73/61.2; 210/198.3; 210/658; 422/68; 436/2; 436/60; 436/162

[58] Field of Search ............ 422/68, 69, 70; 436/2, 436/60, 140, 141, 161, 162; 73/61.2, 61.1 C, 64, 54; 210/658, 198.3

[56] References Cited

U.S. PATENT DOCUMENTS

| | | | |
|---|---|---|---|
| 2,302,224 | 11/1942 | Jones | 73/64 |
| 3,049,964 | 8/1962 | Miller et al. | 73/64 |
| 3,413,842 | 12/1968 | Hecker | 73/61.1 C |
| 3,777,163 | 12/1973 | Aubin et al. | 73/61.1 C |
| 3,922,431 | 11/1975 | Radmacher et al. | 210/198.3 |
| 3,994,587 | 11/1976 | Yamamoto et al. | 356/73 |
| 4,013,364 | 3/1977 | Nakano et al. | 356/73 |
| 4,145,139 | 3/1979 | Nakamura et al. | 356/73 |
| 4,155,833 | 5/1979 | Gleim | 208/309 |
| 4,544,271 | 10/1985 | Yamamoto | 256/328 |

FOREIGN PATENT DOCUMENTS

| | | | |
|---|---|---|---|
| 13274 | 6/1968 | Japan | 436/60 |
| 146040 | 11/1980 | Japan | 436/162 |
| 989481 | 1/1983 | U.S.S.R. | 436/60 |

OTHER PUBLICATIONS

Poirier et al., *Energy Sources*, vol. 7, No. 2, pp. 165–177 (1983).

Primary Examiner—Barry S. Richman
Assistant Examiner—Robert J. Hill, Jr.
Attorney, Agent, or Firm—R. L. Graham

[57] ABSTRACT

Apparatus and method for determining the tendency of hydrocarbon liquid to foul equipment includes a horizontal polymeric membrane made from polymers containing polar atoms, a light source for scanning hydrocarbon liquid sample on the membrane, and means for measuring the difference in light reflected by the asphaltene ring and the membrane matrix. Energy sources other than light may be employed.

9 Claims, 2 Drawing Sheets

HIGH-FOULING CRUDE OIL

LOW-FOULING CRUDE OIL

APPARATUS FOR DETERMINING FOULING TENDENCY OF LIQUID HYDROCARBONS USING POLAR POLYMERIC MEMBRANES

CROSS REFERENCE

This application is a Continuation-In-Part of U.S. Ser. No. 910,910, filed Sept. 24, 1986, which is a Continuation-In-Part of U.S. Ser. No. 830,386, filed Feb. 18, 1986, which is a Continuation-In-Part of U.S. Ser. No. 723,958, filed Apr. 15, 1985.

BACKGROUND OF THE INVENTION

1. Field of the Invention

The present invention relates to an apparatus and method for determining the tendency of liquid hydrocarbon streams to foul equipment and more particularly to an apparatus and method for determining oil-asphaltenes incompatibility and related fouling tendency.

2. Related Art

Petroleum streams, depending on their asphaltene and oil characteristics, have different precipitating and fouling characteristics with regard to heated oil refinery surfaces. The problem of predicting the offending substances in a particular stream such as crude oil which foul heat exchanger equipment in oil refineries and petrochemical plants has been virtually unresolved. Equipment fouling by heated hydrocarbon streams which result in inorganic and carbonaceous deposits on heat exchanger surfaces leads to a blockage of flow and a decrease in heat transfer. Both conditions severely reduce heat efficiency in the processing of the crude oil. A reliable technique for identifying the problem crudes would enable the operator to apply remedial measures such as removing the offending substances or by adding antifouling agents.

There are a number of methods and devices available for determining the rates of fouling of petroleum streams. Conceptually, they are all similar in that they attempt to measure the change in heat transfer from a heated surface to a test fluid. These methods are either not reliable or are time consuming.

One approach is to use a test unit which is designed to allow measurement of the fluid temperature at the exit of the heat-exchanger while the metal temperature of the heated tube is controlled. This configuration provides for close simulation of refinery and petrochemical plant heat-exchanger operations and provides for measurement of the significant effect of fouling which is indicated by the reduction of heat transfer. The test unit provides for a thermal fouling evaluation of the crude oil in an accelerated test which is designed to reproduce the fouling problem experienced in a refinery over several months. Acceleration is provided by carrying out test operating temperatures higher than those in a particular refinery unit, so that the prospective level of fouling can be produced in a reasonable period of time (usually 3-4 hours). Heat transfer data is obtained by holding the heater tube at a constant temperature while measuring the change in the liquid outlet temperature. As fouling progresses, i.e., carbonaceous deposits build up on the heater tube surface, a decrease in the fluid outlet temperature results. The change in liquid outlet temperature with time provides the basic heat data required for comparative evaluation of untreated material and additive-treated material. The rate of change in outlet liquid temperature versus time shows relative fouling tendencies.

Current test equipment is only capable of measuring the overall tendency of heated petroleum stream to foul refinery equipment and cannot predict which are the offending substances or fractions.

An article entitled "Thin-Layer Chromatographic Method for Determination of Asphaltene Content of Crude Oils and Bitumens", authored by Poirer and George, published in 1983 *Energy Sources*, Volume 7, No. 1, discloses a method which involves determination of asphaltenes content by conventional thin-layer chromatographic (TLC) procedures, extraction of the asphaltenes by toluene, and colorimetric determination of the asphaltenes. This process involves the use of TLC tank with developer solvent. Although described as a fast method, the article states that about 8 hours are required to analyze 15 samples. Moreover, this method mesures asphaltene content and not asphaltene/oil incompatibility which is the case of fouling.

Hence, it is an advantage of the present invention that an improved method and apparatus which will rapidly indicate the fouling tendency of asphaltene containing petroleum streams is provided. It is a particular advantage the present invention can be employed in the refinery in a very short period of time by unit operators without extensive chemical training. These and other advantages and features will be apparent from the following test.

SUMMARY OF INVENTION

The method according to one embodiment of the present invention comprises:

(a) depositing a liquid hydrocarbon sample onto a TLC plate in a horizontal position;

(b) permitting the sample to spread radially thereon whereby the incompatible asphaltenes form a ring on the surface of the polymeric membrane plate and the compatible components invade the matrix of the polymeric membrane;

(c) scanning the spread circular chromatogram with an energy source (preferably light);

(d) measuring a property (preferably reflected light) which distinguishes the incompatible asphaltenes ring from the matrix;

(e) comparing the property of the matrix with that of the incombatible asphaltene ring, the value of which provides an indication of the tendency of the liquid hydrocarbon to foul equipment.

The present invention in one aspect also relates to an apparatus which employs a chromatographic separation on polymeric membrane and optics for measuring the tendency of liquid hydrocarbons to foul. The apparatus comprises, in a preferred embodiment:

(a) a polymeric membrane for receiving a sample of the liquid hydrocarbon on an exposed surface thereof, (b) a light scanner for scanning across the chromatogram on the polymeric membrane, (c) a light sensor for measuring the light transmitted or reflected by the sample on the membrane, and (d) means for comparing the light transmitted or reflected by incompatible asphaltenes deposited on the membrane with the matrix zone within the sample receiving portion. Matrix refers to the invaded zone without the separated incompatible asphaltenes. The matrix may be inside and/or outside the asphaltene ring, depending on the crude oil.

In a preferred embodiment the optical information is converted into a logic level pulse representative of the light transmitted or reflected. These signals during each scan provide a profile of the liquid hydrocarbon sample. By integrating the area of the profile corresponding to the asphaltene separated portion (matrix profile being 0), the characteristic reading of the samples tendency to foul is obtained. This value can be compared to a standard value of known hydrocarbons.

It has been discovered that the incompatibility of asphaltenes in the liquid hydrocarbon is a measure of the tendency of the liquid to foul. The incompatibility may be detected by the use of polymeric membranes. Depositing a drop of the hydrocarbon stream on the membrane produces rings of light (non-fouling) components and dark (fouling) components precipitated on the membrane film, usually in the form of a dark ring. These ring formations may be enhanced by the use of diluents, paraffinic solvents, or asphaltene antisolvents such as n-heptane, iso-octane, and decane or solvents containing polar atoms such as alcohols, ketones, amines, ether, etc.

The intensity and area of the asphaltene ring when optically compared to the light region provides a reliable indication of the fouling tendency of the liquid hydrocarbon. The optical data may be converted to digital output - the value of which classifies a hydrocarbon liquid according to its tendency to foul.

In a preferred embodiment, the method comprises the following steps:

(a) depositing a sample amount (usually one drop) of liquid petroleum from the hydrocarbon stream being monitored onto a flat horizontal surface of a polymeric membrane which has the property of chromatographic separation of the incompatible asphaltene from the sample by adsorption;

(b) providing sufficient time for radial outward migration of the sample on or in the membrane (from around 5 minutes to around 2.0 hours) to permit an asphaltene ring to form;

(c) scanning the migrated sample with a light source; and (d) measuring the reflected light throughout the scanned portion.

The difference or ratio of light reflection between the asphaltene ring and the remainder of the sample in or on the membrane provides the indication of fouling tendency of the hydrocarbon stream from which the sample was taken.

Once the petroleum stream has been identified as fouling according to the present invention, it can be treated to reduce fouling by incorporating a small quantity of an antifouling agent, such as the well known dispersants used in the refining industry. Thus one aspect of the present invention is a method for reducing the fouling tendency of petroleum streams flowing through a vessel comprising:

DESCRIPTION OF THE PREFERRED EMBODIMENTS OF THE INVENTION

Figure 1:
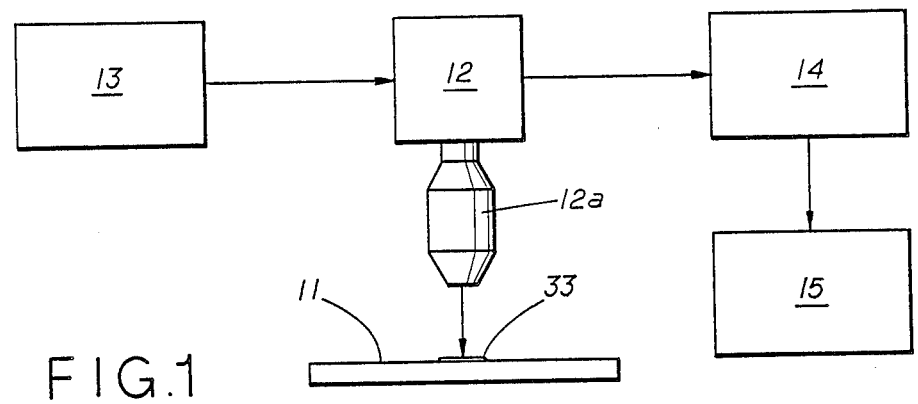
FIG. 1 is a flow diagram schematically illustrating the operation of the apparatus constructed according to the present invention.
Figure 2:
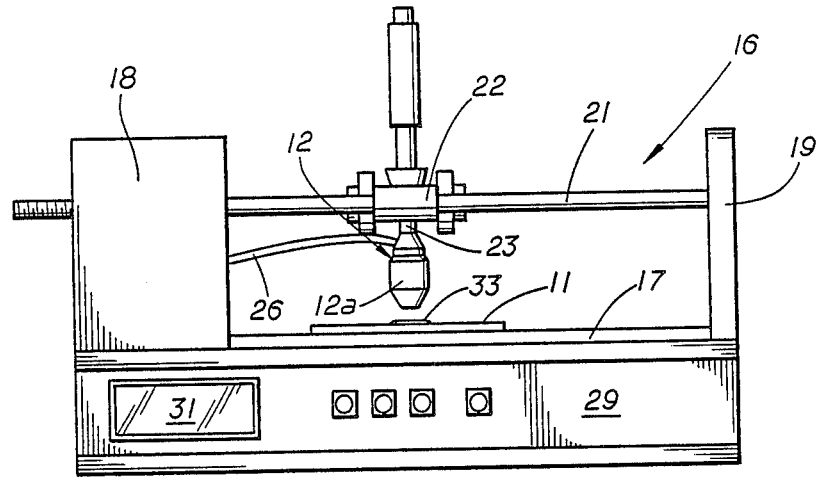
FIG. 2 is a side elevational view of the apparatus constructed according to the present invention.
Figure 3:
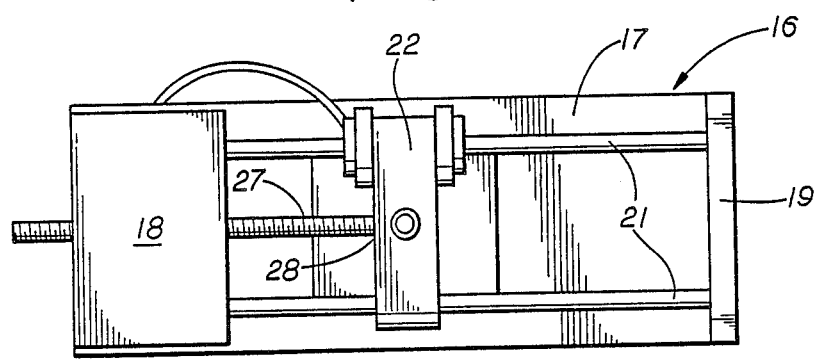
FIG. 3 is a top plan view of the apparatus shown in FIG. 2.

Referring to FIGS. 1, 2, and 3, the apparatus of the present invention comprises a polymeric membrane 11 for receiving a drop of hydrocarbon liquid, a scanner 12 including light source head 12a and means 13 for moving the scanner 12, means for measuring transmitted or reflected light which may be a part of scanner 12, a data acquisition unit 14 which includes means for comparing transmitted or reflected light in the scanned region and means 15 for converting the data to useful information (e.g. a signal such as a digital signal indicative of the tendency of a liquid hydrocarbon to foul). Optionally, the apparatus may include means for displaying the results.

As shown in FIGS. 2 and 3, the scanner 12, membrane 11, and means for moving the light scanner are shown as a single unit 16. The unit 16 comprises briefly a support platform 17, a main housing 18 mounted on one end thereof and an end frame member 19 mounted on the other end thereof. Disposed above the platform 17 and extending in parallel relationship with one another are polished rods 21 which interconnect the main housing 18 and frame member 19. A bar 22 is slideably mounted on the polished rods 21 and provides means for supporting the scanner 12. A vertical rod 23 extends through a central hole of the bar 22 and is secured thereto by set screws (not shown). The scanner 12 is mounted to the lower end of the rod 23. The rod 23 may be provided with telescopically threaded members with micrometer means (not shown) for adjusting the vertical elevation of the scanner 12 in relation to the polymeric membrane 11.

In a preferred embodiment, the scanner 12 comprises a light source and a sensor for measuring the reflected light and converting that into a digital signal which is transmitted to the data acquisition unit 14 by lines 26.

The means for moving the scanner 12 assembly horizontally to scan the sample on the polymeric membrane 11 is provided by conventional motor and gear assembly. A threaded shaft 27 is mounted by suitable bearings in main housing 18 and has its outer end secured to the bar 22 as at 28. Thus rotation of the shaft 27 through a conventional threaded drive within housing 18 moves the scanner assembly along the polish rods 21. The shaft motor and gear reducers should be designed to provide a relatively slow rectalinear motion. About 2 inches per minute is satisfactory for most applications.

The electronics and circuitry for the instrument including units 14 and 15 may be housed in box 29 underlying support 17. Optionally, the apparatus may include a digital output 31 for indicating the level of the tendency of the sample to foul according to a calibrated scale.

The scanner 12 may be in the form of an industrial digital bar code such as those commercially available from Hewlett Packard with Circuitry for converting the reflected optical information to a logic level pulse representative of the reflected light. Alternatively, the scanner 12 may include a separate light source and a high resolution optical reflective sensor, such as Hewlett Packard HEDS-1000. The device includes a light emitter and sensor for sensing the visible light from 600–700 nm.

The pulse signal from the scanner 12 is transmitted to a data acquisition unit such as Hewlett Packard 3421A which converts the pulses into meaningful information that can be represented digitally or graphically by the use of a conventional computer and plotter.

The polymeric membrane 11 is preferably polymeric porous membrane or film made from polymers, preferably thermoplastics such as polyolefins, containing polar atoms such as fluorine, chlorine, oxygen and nitrogen. A preferred membrane is made from polyvinylidine difluoride (PVDF). This membrane (Metricel GAN6) is commercially available from:

Gelman Science, Inc.
Ann Arbor, Mich., 48106.

Other polymeric membranes such as polysulphone, Metricel GA6 or GA8 or Tuffryn 1+T−100 can also be used. Other membrane materials may include cellulose acetate and cellulose nitrate.

The size of the membrane may vary, but a size from 10×10 cm to 5×5 cm, with a thickness of 0.2 mm will be satisfactory for most applications. The membrane is maintained on a glass or impervious plastic support plate.

In practice, the hydrocarbon sample may be used in diluted form (with an asphaltene antisolvent) or undiluted form (neat), on a dry polymeric membrane, or on a membrane wet with the asphaltene antisolvent. A procedure which has provided good results is in accordance with the examples described herein.

In operation, a drop of the liquid hydrocarbon is deposited on a flat surface of a polymeric membrane. A conventional disposable transfer pipet (Pasteur type 5 ¾") provides means for depositing drops of substantially the same volume on the plate. After a predetermined period of time in which the sample spreads onto or into the membrane media (usually from 5 minutes to 2 hours), the scanner 12 is passed over the plate scanning the full scope of its radial migration on the membrane.

Tests indicate that the nonfouling components including soluble asphaltenes (compatible asphaltenes) invade by capillary action into the polymeric membrane 11, whereas the incompatible asphaltenes plate out on the surface of the polymeric membrane 11. Thus the incompatible asphaltenes, being at or near the surface of the polymetric membrane 11, are effective light absorbers whereas the other components penetrated into the polymeric membrane 11 and the membrane itself reflects light from the light source.

Figure 4:
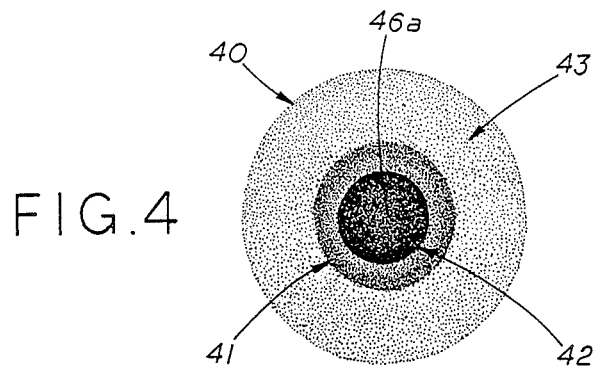
FIG. 4 is an enlarged top plan view of an asphaltene containing hydrocarbon sample after migration on the membrane.
Figure 5:
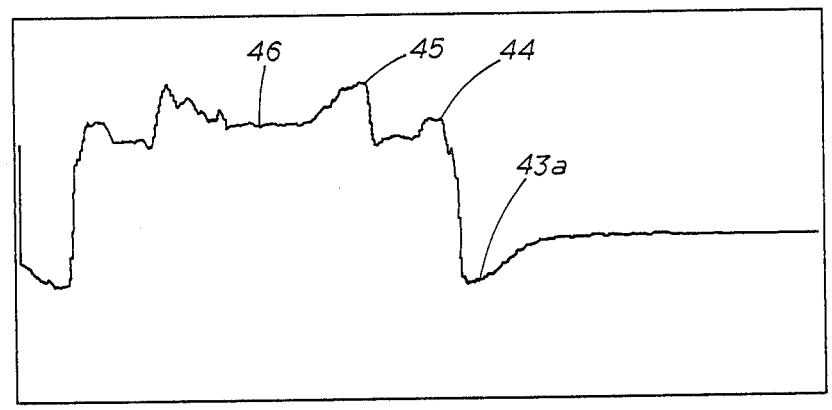
FIGS. 5 and 6 are graphs of a high fouling crude and a low fouling crude, respectively, as measured by the apparatus of the present invention.

The mechanisms involved in distinguishing high fouling crude from low fouling crude will be described with reference to FIGS. 4, 5, and 6. A sample drop 40 as it appears on the membrane 11 is illustrated in amplified form in FIG. 4. The drop, after spreading comprises an invaded region indicated at 41 and a dark ring region indicated by ring 42. A light region 43 outside perimeter of region 41 sometimes develops. It is believed that this region consists of very light hydrocarbons which separate from the intermediates. Depending on the amount of incompatible asphaltenes in the sample, the interior 46a of the dark asphaltene ring 42 may be dark (as illustrated) indicating asphaltenes or may be lighter. The light regions 41 and in some samples region 46a are referred to herein as the matrix regions and contain the compatible (nonfouling) components.

The light scanner 12 determines the magnitude of the reflected light in both the matrix regions and the incompatible asphaltenes region. The reflected light increases downward and decreases upward as viewed in FIGS. 5 and 6. Viewed another way, absorbed light increases upwardly on the plots of FIGS. 5 and 6. Comparing the plot of FIG. 5 with the sample of FIG. 4, it can be seen that as the scanner 12 moves from right to left, it first encounters a high light reflected area as at 43a which indicates the light hydrocarbon fractions in region 43 of the sample. When the scanner 12 encounters the periphery of region 41 of the sample, the reflected light decreases rapidly to 44 and levels off providing a reading for matrix region 41. Upon encountering the asphaltene ring 42, the reflected light again decreases to 45 and again increases as the scanner 12 enters the central matrix portion 46a. Note that reflected light indicated by reading of 46 is slightly less than that indicated by reading 44 indicating that the incompatible asphaltenes are present in region 46a. Continued movement of the scanner 12 to the left half of the sample provides a generally symmetrical plot of the light reflecting characteristic of the sample on the membrane. The key indicator of a crude's tendency to foul is provided by the area of the plot above the base line 44 (matrix region) which is a function of both the measure of light reflected and the areal extent of ring 42. If this area is large as in FIG. 5, the crude will be found to have a high tendency of fouling. However, if it is small as illustrated in FIG. 6 the tendency to foul will be low. This may be viewed as the volume above the base lines since light reflected is based on the area of the ring and the amplitude of light reflected. In a preferred embodiment the data acquisition unit is programmed to integrate the area above base line 44 and 46 and convert that measurement to a digital reading calibrated according to known fouling tendency.

This reading then can be compared to a standard scale based on crudes of known fouling tendencies. For example, several samples were analyzed by the apparatus of this invention and by the Thermal Fouling Tester (TFT) which is described in Applicant's copening Application filed on Apr. 8, 1986 Ser. No. 849,600, the contents of which is incorporated herein by reference.

The following 0-100 scale was developed based on comparing the Apparatus reading and TFT readings.

| Fouling Tendency | Fouling Index of Apparatus | TFT Δ T(°F.) |
|---|---|---|
| low | 0–20 | 0–15 |
| medium | 21–40 | 16–39 |
| high | 41–100 | 40+ |

The above scale was developed by calibrating the apparatus with TFT readings based on hundreds of samples.

The present invention thus determines the tendency of hydrocarbon liquids to foul equipment and the results correlate well with the tedious TFT method. Note that the apparatus reading does not correspond to the ΔT of the TFT. However, the groupings (high, medium, low) correlated very well.

As used herein, asphaltene incompatibility of the total petroleum stream is indicative of the susceptibility of asphaltenes to separate from the oil, adhere to the heated metal surface, transfer into coke-like material and result in fouling of the metal surface. The greater the incompatibilty of the asphaltenes in the oil, the higher the fouling tendency of the hydrocarbon stream.

Asphaltenes present in crude oils have high average molecular weight (Mn=900-1300) and a very broad molecular weight distribution. Gel permeation chromatographic (GPC) characterization of two crude oil asphaltenes molecules indicates the presence of molecular weight as high as 5000.

Although best results are generally obtained with diluted samples, in some cases, it may suffice merely to use neat samples.

Paraffinic or polar solvents or their blends can be used to dilute the samples and these are effective over a broad range of oil/solvent ratios. Asphaltene is substantially insolvent in these materials. These asphaltene antisolvents must be a low molecular weight, low viscosity and have low boiling characteristics to allow rapid migration on the polymeric membrane.

The paraffinic antisolvents are preferably up to $C_{18}$ straight or branched alkanes. Usually $C_5$ to $C_{10}$, e.g., suitable antisolvents include pentane, isopentane, hexane, 2-methyl hexane, n-heptane, octane, nonane, decane, isooctane and the like.

The polar antisolvents cover a broader spectrum of materials. The present polar solvents are organic compounds which are liquids under the conditions of use. The term "polar" refers to atoms such as oxygen, sulfur, oxygen, halogens and nitrogen. A partial listing of suitable polar antisolvents includes alcohols such as, isobutanol, 2-pentanol, isoamyl alcohol; ketones such as acetone; methyl ethyl ketone; ethers such as diethyl ether, methyl propyl ether; esters such as methyl formate, butyl formate, methyl acetate, methyl propionate; glycol ethers, such as ethylene glycol monomethyl ether, ethylene glycol diethyl ether; heteroatom compounds such as furan, tetrahydrofuran, furfural, methyl pyridine, and the like. Mixtures of hydrocarbon and polar materials are desired antisolvents for petroleum streams containing functional groups. The selection of a suitable antisolvent depends on the atmospheric temperature of the polymeric membrane. For example, in the laboratory (20° C.) n-heptane or n-decane were used satisfactorily. On-site testing in cold weather, may require pentane or isoctane, whereas a refinery site in hot weather such as in Texas or Louisiana where the TLC glass plate will have high temperature, may require a high boiling antisolvent such as nonane or decane.

Other chemicals may be used to enhance the separation of incompatible asphaltenes and from the hydrocarbon oil fraction. These include asphaltene demulsifiers and other chemicals which will react chemically or physically with asphaltenes to (a) decrease asphaltene solubility or dispersion in oil and/or (b) increase separation of the asphaltenes, and/or (c) increase asphaltenes adhesion or absorption to the TLC material (e.g., silica gel or polymer membrane). Such chemicals include acids, bases, and organic-metallic compounds.

The present invention of fouling characterization is simple and easy to use in the laboratory and in the field for monitoring crude oil fouling characteristics routinely by nontechnical personnel. The method may be used in three ways: (a) use of antisolvent in the oil sample, (b) use of antisolvent on the polymeric membrane, and (c) use of neat sample. The use of antisolvent is preferred however since it appears to be the most versatile in the variety of crudes capable of testing.

(a) As described above, the antisolvent can be added to and blended with the crude oil. The blend (one drop) then is deposited on the membrane. The spreading of the sample to form a circular invaded zone will develop in a very short time. The sample is then scanned and the rflected light measured as described previously. FIGS. 5 and 6 are representative of the instrument output plot.

The ratio of antisolvent to oil will obviously vary from crude to crude, not only for the enhancement of the insolubility of the asphaltenes but also to reduce the viscosity of the crude to an extent to make it operable with the polymeric membrane. Light and medium crudes require only a few minutes for development of the chromatographic pattern, whereas heavy crudes, such as the California crudes, may require a few hours.

The antisolvent is preferably added to the oil in a ratio ranging from 0.2:1 to 1:0.2, more preferably 0.5:1 to 1:0.5 (antisolvent:oil ratio). The use of the correct oil/antisolvent ratio is important for the successful separation of asphaltene and oil on the membrane. When adding the antisolvent to the oil, the antisolvent will insolubilize the asphaltene, especially the low molecular weight part of the asphaltenes and produce a very clear and well defined asphaltene ring on the TLC plate, which can then be easily related to fouling characteristics with greater assurance by the unit operator using the test. The preferred antisolvents include $C_5$-$C_{10}$ hydrocarbons straight and branched alkanes at a ratio wherein the hydrocarbon liquid comprises the major volume proportion. The preferred system comprises from 10 to 30 volume percent of pentane, isopentane, hexane, 2 methyl hexane, n-heptane, octane, nonane, decane, isoctane, or mixtures of these and 70 to 90 volume percent of the liquid hydrocarbon.

(b) The present method can also be used by simply adding one or a few drops of the antisolvent onto the dry membrane (just to wet the thin film) and then applying a drop of the oil onto the wet film and allowing the chromatogram to develop followed by scanning as described above. This method is particularly suitable for on-site tests in the refinery. It is also possible to use a combination of the two embodiments of the present invention, which may be useful with very heavy crudes.

(c) The neat crude oil sample may be deposited directly on the membrane, followed by the steps described above.

The following procedure was used in Examples I, II, and III to produce the several thin layer chromatograms:

EXPERIMENTS

The following two forms of the apparatus was used, both employing reflected light as the operative mechanism:
(1) Polymeric Membrane:
    Metricel GAN6, Gelman Science Inc.,
    Ann Arbor, Mich., 48106
Scanner:
    Hewlett Packard Optical Reflective Sensor
    Model HEDS-1000
Data Acquisition:
    Hewlett Packard 3421A
Unit Plotter:
    by Hewlett Packard UX Integral Personal Computer of Hewlett Packard programed for graphics.
(2) A second unit was provided with the same membrane and scanner. Instead of the plotter, a computer capable of integrating the area above the matrix reading was built into the apparatus and provided only with digital output of the fouling index based on the scale decribed above.

EXAMPLE 1

A drop of a high fouling crude oil (as determined by TFT) with antisolvent (1 part volume decane plus 4 parts crude) was placed on the dry polymeric membrane and permitted to migrate for 60 minutes at room temperature. The chromatogram on the polymeric membrane then was scanned with instrument (1) above and the graph shown in FIG. 5 was produced. Note that the plot of FIG. 5 corresponds to the sample of FIG. 4 previously described. The fouling index as read by the Apparatus was 98, indicating a high fouling crude.

EXAMPLE 2

Figure 6:
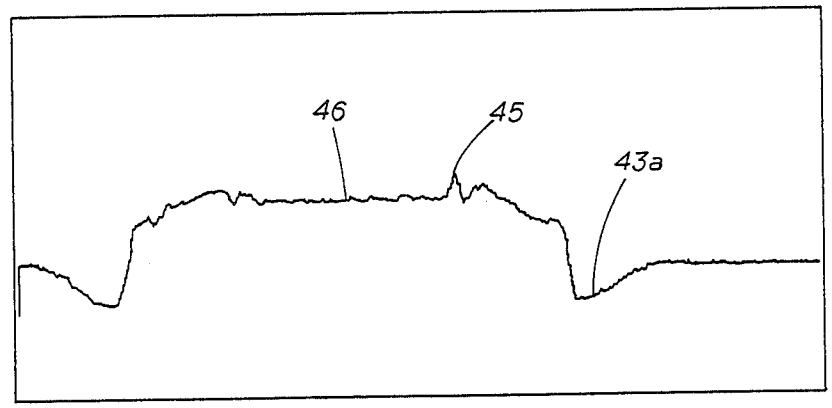

The same test was run using a low fouling crude (as determined by TFT) which gave the plot of FIG. 6. This sample gave a fouling index reading of 2 by Apparatus 1, indicating a low fouling crude. Note that the reference numerals on FIG. 6 correspond to description with reference to FIG. 5, except that no asphaltene ring is present. In FIG. 6, the reference line is 46.

What is claimed is:

1. An apparatus for measuring the tendency of a hydrocarbon liquid to foul equipment which comprises:
    (a) a polymeric membrane for receiving a sample of a hydrocarbon liquid on an internal portion thereof, said membrane being capable of separating incompatible asphaltenes from compatible components of a sample of a hydrocarbon liquid to form an incompatible asphaltene ring region and a matrix region of compatible sample components on or in the internal portion of said membrane;
    (b) a light source adapted to scan the internal portion of the membrane;
    (c) means for measuring light from the light source which has been affected by the internal portion of the polymeric membrane;
    (d) means for comparing measured light corresponding to an asphaltene ring region of the internal portion of the membrane with measured light corresponding to a matrix region of the internal portion of the membrane and generating a corresponding comparison signal; and
    (e) means for receiving a comparison signal from the comparing means and converting such a comparison signal into an electric signal indicative of the tendency of a liquid hydrocarbon to foul equipment.

2. An apparatus for measuring the tendency of a hydrocarbon liquid to foul equipment which comprises:
    (a) a substantially horizontal polymeric membrane for receiving a sample of a hydrocarbon liquid on an internal portion thereof, said membrane being capable of separating incompatible asphaltenes from compatible components of a sample of a hydrocarbon liquid to form an incompatible asphaltene ring region and a matrix region of compatible sample components on or in the internal portion of said membrane;
    (b) a light source adapted to scan the internal portion of the membrane;
    (c) means for measuring light from the light source which is transmitted through or reflected by the internal portion of the polymeric membrane;
    (d) means for comparing light transmitted through or reflected by an asphaltene ring region of the internal portion of the membrane with light transmitted through or reflected by a matrix region of the internal portion of the membrane and generating a corresponding comparison signal; and
    (e) means for receiving a comparison signal from the comparing means and converting such a comparison signal into an output signal indicative of the tendency of a liquid hydrocarbon to foul equipment.

3. The apparatus of claim 2 wherein the output signal is a digital signal.

4. The apparatus as defined in claim 2, wherein the comparing means includes means for measuring (i) the area and intensity of light reflected by an asphaltene ring region of the internal portion of the membrane and (ii) the area and intensity of light reflected by a matrix region of the internal portion of the membrane.

5. The apparatus as defined in claim 2 wherein the membrane is a film made of a thermoplastic selected from polyolefins containing polar atoms.

6. The apparatus as defined in claim 5 wherein the film is made of polyvinylidine difluoride.

7. The apparatus of claim 2 wherein the means for measuring light comprises means for measuring reflected light; and the comparison means comprises means for comparing reflected light from an asphaltene ring region of the internal portion of the membrane with reflected light from a matrix region of the internal portion of the membrane.

8. The apparatus of claim 7 wherein the means for measuring reflected light includes a light sensor for measuring light reflected from the internal portion of the membrane through one pass of the light source over the internal portion of the membrane and means for converting measured reflected light into electric signals, and wherein the comparison means includes means for comparing electric signals corresponding to an asphaltene ring region of the internal portion of the membrane with electric signals corresponding to a matrix region of the internal portion of the membrane.

9. The apparatus of claim 8 wherein the comparison means includes means for comparing (i) the average value of electric signals corresponding to an asphaltene ring region of the internal portion of the membrane multiplied by the area of such an asphaltene ring region with (ii) the average value of electric signals corresponding to a matrix region of the internal portion of the membrane multiplied by the area of such a matrix region.

* * * * *